United States Patent [19]
Van Es

[11] Patent Number: 6,100,045
[45] Date of Patent: Aug. 8, 2000

[54] DETECTION OF ANALYTES USING ELECTROCHEMISTRY

[75] Inventor: Remco Maria Van Es, Giessenburg, Netherlands

[73] Assignee: DSM N.V., Te Heerlen, Netherlands

[21] Appl. No.: 09/020,561

[22] Filed: Feb. 9, 1998

[30] Foreign Application Priority Data

Feb. 10, 1997 [EP] European Pat. Off. .............. 97200368

[51] Int. Cl.⁷ ......................... G01N 33/53; G01N 33/566; G01N 27/26; G01N 27/00; C12N 1/36
[52] U.S. Cl. ........................... 435/7.1; 435/7.1; 435/7.9; 435/7.93; 435/7.94; 435/6; 435/289.1; 435/290.1; 435/817; 436/501; 204/403; 204/418; 204/153.12
[58] Field of Search ........................... 435/7.1, 7.9, 7.93, 435/7.94, 6, 289.1, 291, 817; 436/501; 204/403, 418, 153.12

[56] References Cited

U.S. PATENT DOCUMENTS

| | | |
|---|---|---|
| 4,357,311 | 11/1982 | Schutt . |
| 4,978,610 | 12/1990 | Forrest et al. .............................. 435/7 |
| 5,391,272 | 2/1995 | O'Daly et al. ........................... 204/153 |
| 5,541,072 | 7/1996 | Wang et al. ............................. 435/7.21 |
| 5,554,339 | 9/1996 | Cozzette et al. ........................... 422/50 |

FOREIGN PATENT DOCUMENTS

| | | |
|---|---|---|
| 0 352 138 | 7/1989 | European Pat. Off. . |
| 90/05300 | 5/1990 | European Pat. Off. . |
| 0 525 723 | 5/1997 | European Pat. Off. . |
| 859230 | 8/1998 | European Pat. Off. ................. 27/327 |
| 2 289 339 | 11/1995 | United Kingdom . |
| 92/14138 | 8/1992 | WIPO . |
| 95/31725 | 11/1995 | WIPO . |

OTHER PUBLICATIONS

D. Huet et al., "Automatic Apparatus for Heterogeneous Enzyme Immunoassays Based on Electrocatalytic Detection of the Enzyme and Electrochemical Regeneration of the Solid Phase", Analytica Chimica Acta, vol. 272, No. 2, Feb. 12, 1993, pp. 205–212.

C. Gyss et al., "Enzymatic Electrocatalysis as a Strategy for Electrochemical Detection in Heterogeneous Immunoassays", Analytical Chemistry, vol. 59, No. 19, pp. 2350–2355.

Y. Xu et al., "Solid–phase Electrochemical Enzyme Immunoassay with Attomole Detection Limit By Flow Injection Analysis", Journal of Pharmaceutical and Biomedical Analysis, vol. 7, No. 12, 1989, pp. 1301–1311.

*Primary Examiner*—Nita Minnifield
*Assistant Examiner*—Padma Baskar
*Attorney, Agent, or Firm*—Morrison & Foerster, LLP

[57] ABSTRACT

The present invention relates to diagnostic assays whereby the detection means is based on electrochemical reactions. This means that the label to be detected provides an electric signal. Preferred labels are enzymes giving such a signal. Provided is a flow cell whereby a solid phase is provided in a flow stream of the sample, in close proximity to a working electrode to detect any electrical signal. In a typical embodiment, a sample is mixed with molecule having specific binding affinity for an analyte of which the presence in the sample is to be detected, whereby said specific binding molecule is provided with a label. The conjugate of labelled specific binding molecule and analyte is then immobilized on the solid phase in the vicinity of the working electrode, the flow cell is rinsed with a solution and afterwards a substrate solution for the label (an enzyme) is provided upon which an electrical signal is generated and can be detected by the working electrode. The methods and devices of the present invention are particular useful for liquids which comprise many substances that may disturb measurement in conventional assays. The design of the flow cell allows for removal of said interfering substances before measurement. In a preferred embodiment at least part of the solid phase is provided in the form of magnetic beads. In this embodiment the solid phase can be mixed with the sample thereby creating a longer reaction time, a better sensitivity and a higher speed of the assay.

19 Claims, 6 Drawing Sheets

DETECTION OF ANALYTES USING ELECTROCHEMISTRY

INTRODUCTION

The invention detailed in this document describes a novel assay technique and apparatus for determining the presence and/or concentration of analytes in complex sample matrices. The invention utilises molecules having specific binding affinities for other molecules (usually the analyte(s) to be detected). Such assays are generally termed diagnostic assays, although they are not necessarily concerned with diagnosing illnesses or other such physical conditions.

The diagnostic field is a relatively well developed area in which many different assay systems and test formats have been developed for a wide range of analytes including hormones, pathogens (including viral and bacterial sources) drugs and antibiotics. The molecules having specific binding affinities for the analytes to be detected include antibodies (monoclonal, polyclonal), antibody fragments, receptors, nucleic acids or ligands. Many different binding molecules specific for a whole range of analytes are now readily available or can be routinely produced. In the context of this patent, the term 'immuno-' refers to any of the specific binding components listed above unless otherwise stated.

These assays operate on the principle of quantifying the extent of specific binding of the test analyte to the binding component. Therefore, care must be taken to ensure that substances that can affect the signal to be measured and are present as a result of non-specific binding interactions are first removed. Most assay procedures therefore include one or more washing steps, intended to remove such substances.

Many sample liquids, such as whole blood, milk and saliva may contain substances that can cause interference to the assay signal. Consequently, many assays lack the required sensitivity, speed and ease-of-use for a particular application.

These are important criteria for the development and operation of a successful assay procedure and few test systems are currently commercially available that fulfil all these requirements in a satisfactory manner. Often assay sensitivities are insufficient (often analyte concentrations as little as microgrammes per litre or less must be detectable which is difficult to achieve in the presence of interferents). In the case when assay sensitivities are sufficiently high, this is normally at the expense of a number of washing and/or separation steps, necessitating the assay to be performed by trained personnel. Moreover, the various steps necessary to reach the required sensitivity and/or specificity result in prolonged assay times, unacceptable for many test applications.

ASSAY FORMATS INCORPORATING SPECIFIC BINDING COMPONENTS

A short summary of two of the most common specific binding assay formats is given below.

Sandwich Type Assay

A 'capture' molecule with specific binding properties (e.g. an antibody or receptor molecule) for a given analyte is immobilised onto a solid phase support (e.g. nitrocellulose membrane, plastic microtiter well or carrier beads). The immobilised molecule is then exposed to a sample suspected of containing the analyte of interest. Under appropriate conditions, the analyte will bind and hence be immobilised by the capture molecule. Separation of bound and unbound analyte is achieved with a washing step. A second binding component, labelled with a tracer molecule (e.g. enzyme, radio label, fluorescent label or colloidal sol particle) with specific affinity for the analyte is allowed to bind to the analyte-capture molecule complex. A further washing step is followed by the addition of enzyme specific substrate solution. The magnitude of the generated signal is directly proportional to the amount of analyte present.

Competitive or Non-competitive Inhibition Assay

A molecule with specific binding properties (binding partner) for a given analyte is immobilised onto a solid phase support as described for the sandwich type assay. Analyte present in a sample competes for these specific binding sites with an added analyte analogue, conjugated to a label (e.g. enzyme label, radio label, fluorescent label or colloidal sol particle). After a washing step, the label is detected according to appropriate techniques. The magnitude of the signal generated is inversely proportional to the amount of analyte present in the sample.

COMMON DETECTION METHODS

The presence of a label can be determined by several methods. For example, the presence of an enzyme label can be determined by chromogenic, fluorescent, luminescent or electrochemical means.

Chromogenic based assays generally involve simple laboratory procedures but suffer from long incubation times and relatively poor levels of sensitivity. Nevertheless, this approach is routinely used. One approach of particular interest and wide-spread use are the so-called 'dipstick' tests. These test devices incorporate, within their design, all of the assay components necessary for analyte detection coupled to a wicking device and is a one-step process. The simplicity of device operation and low costs involved have resulted in a large market for this type of product. Assays of this type have been described in the literature.

Electrochemical assays focus on monitoring electrochemically active substances, either generated or consumed by a redox or other enzyme located at the surface of a suitable electrode. A very well known example of this type of assay is the use of the enzyme glucose oxidase, immobilised at an electrode surface, for the determination of glucose in the blood of diabetics. Similarly, cholesterol oxidase can be employed to quantify cholesterol levels in blood or serum. Many types of such 'enzyme electrodes' have been described in the literature.

Ideally, the immobilised enzyme component will be of the redox type. In this way, the electrochemically active species generated or consumed by action of the enzyme can be directly monitored at a suitable electrode surface. Unfortunately, there are many substances of clinical or industrial importance that do not have a suitable redox enzyme counterpart.

Non-redox enzymes can be employed in enzyme electrodes, such as the use of penicillinase for the detection of penicillin. The secondary reaction product of the penicillinase reaction are hydrogen ions which can be detected electrochemically using a standard pH probe. Such systems tend to have very poor sensitivity and are prone to interference.

A potential advantage of electrochemical detection methods over other competing methodologies is the speed in which a measurable signal can be obtained. For example, a traditional ELISA test may require hours in order to develop a measurable signal, compared with minutes for an equivalent electrochemical process. This approach therefore has the obvious advantage of reducing total assay times.

ELECTROCHEMICAL IMMUNOASSAY SYSTEMS

To circumvent these problems and increase the number of analytes that can be detected by electrochemical means, much recent work has focused on the development of electrochemical immunoassay systems. In this approach, a biocomponent that has a specific binding affinity for the analyte of interest, or an analyte analogue, is immobilised within the system (the binding component is usually an antibody or receptor molecule). Analyte detection requires the addition or removal of a tracer material, that has specific binding affinity for the biocomponent, analyte or analyte analogue and which is conjugated to a suitable enzyme label. The amount of immobilised enzyme present serves as a measure of the amount of analyte present in the sample.

Addition of saturating levels of enzyme substrate to the system will result in consumption of substrate at a rate dependent upon the amount of immobilised enzyme present. The depletion of substrate or generation of product can be monitored as appropriate. Typical enzyme labels include glucose oxidase (the reaction by-product, hydrogen peroxide can be detected electrochemically), alkaline phosphatase (the substrate 1-napthyl phosphate is converted to the electrochemically active product naphthol) and horseradish peroxidase.

Electrochemical immunosensor systems described in the literature often lack sensitivity and suffer from poor reproducibility, although the latter factor can be enhanced by repeated use of the same sensor device (Patent GB 2289339). The separation of the working electrode from the counter and reference electrodes has been described in an attempt to increase reproducibility. However, such systems are not user-friendly as all 3 electrodes require separate assembly. Sensor devices designed for repeated use still require periodic replacement, mainly due to fouling effects caused by deposition of materials on the sensor surfaces that can affect device performance. System calibration is necessary each time a new sensor device is used. For these reasons, there are few, if any, examples of truly reliable electrochemical immunosensors currently commercially available.

Current state-of-the-art electrochemical immunosensors reported in the literature generally require total assay times of at least 30 minutes to allow for adequate incubation times, necessary for the specific binding reaction to occur. The use of liquid flow technology to shorten incubation times has been described in the literature. Most of these systems employ a flow channel to sequentially introduce a number of test reagents into the detection unit of a flow cell or flowing liquid system device.

Methods for the improvement of sensitivity and minimisation of assay time using permeable electrodes in flow cell or flowing liquid system devices have been described. However, these systems still do not operate over a useful analytical range of concentrations when assay times are reduced to 10 minutes or less and also suffer from poor reproducibility. Means of ensuring that the electrochemically active endproduct has the opportunity to contact the working electrode device prior to being transported from the system in the flowing liquid stream, thus decreasing the sensitivity of the system have not been addressed. This approach also appears to be susceptible to electrode fouling effects.

EP-A2-0352138 and EP-A2-0525723 both describe the use of a device that incorporates membranes as solid phase supports in conjunction with a solid electrode assembly. These types of electrode assembly are intended as disposable units to be used with appropriate instrumentation.

The invention herein described represents an improvement over existing technology by providing a rapid, sensitive, reproducible method for the electrochemical detection of analytes, without the problems associated electrochemically active interferents that may be present in the sample.

THE INVENTION

The invention provides a method of determining the presence and/or the amount of at least one analyte in a liquid, the method comprises contacting the liquid with both an electrode and a solid phase, wherein the solid phase is no more than 1 mm from the electrode and the solid phase is capable of binding the analyte or an analyte competitor or analyte binder, one of which comprises a label capable of being either directly or indirectly detected by the electrode and detecting the presence, absence or amount of labelled analyte competitor or binder bound to the solid phase, wherein at least part of the solid phase comprises magnetic beads, and the working area of the electrode is the formed by carbon particles containing finely divided platinum-group metal particles.

By analyte competitor or analyte analogue is meant a molecule which is able to bind or has a specific binding affinity to a binding partner which is comparable to the binding of the analyte.

By analyte binder is meant a molecule which is able to bind or has a specific binding affinity for the analyte.

A method and apparatus according to the invention further involves the use of small elements, preferably so-called magnetic beads, as at least part of the solid phase. Magnetic beads are small spheres having a magnetisable core and a coat of a material to which proteins and other materials can be bound (chemically or physical or otherwise). When these beads are coated with a specific binding molecule (sbm) for an analyte, the reaction between solid phase sbm and analyte can be carried out in solution. By providing a labelled specific binding molecule for the conjugate formed a sandwich-type assay is carried out on the magnetic beads. Of course, the skilled artisan knows how to arrange other types of assays. By providing a magnet of any kind in the vicinity of the working electrode, the magnetic beads can be (temporarily) immobilized in the vicinity of the working electrode so that the presence/absence/amount of analyte can be measured by allowing the bound label (preferably) enzyme to generate a measurable signal (preferably by conversion of a substrate). By removing the magnetic field the magnetic beads can be rinsed from the flow cell and they can be discarded or recycled.

Magnetic beads have a very much increased surface area compared to regular solid phases such as filters, so that many more specific binding molecules can be attached to the solid phase leading to improved assays. (Particularly speed and sensitivity). Combinations of different kinds of solid phases will also be useful. Also different kinds of specific binding molecules on different beads or otherwise different solid phases will be useful, for instance for multi-analyte assays.

By providing a flow cell or flowing liquid system in which the sample and following liquids can reproducibly contact an electrode and immobilised assay components, the problems associated with non-specific binding of interfering substances is significantly reduced, probably due to the flow of liquid through the system removing non-specifically bound substances. Specifically bound material should be substantially unaffected by said flow of liquid. Advantageously, the liquid sample is transported from one side of at least the said electrode to the other side thereof, in such a way that the liquid passes said electrode in an essentially non-turbulent manner, such that a substantial proportion of the liquid sample is able to come into contact with said electrode.

Preferably, the electrode devices are mass-fabricated using screen-printing methodology, a simple, cost-effective approach, or other suitable depositioning techniques. The specific binding components of the assay (receptor proteins, antibodies, antibody fragments, strands of nucleic acid or other ligands) can be coated onto the solid phase support by simple protocols. Preferred labels according to this invention are enzymes which act to produce or consume electrochemically active substances to an extent that these reactions are measurable at an electrode surface. Such enzymes include oxidases, reductases, peroxidases and the like, which may originate or be derived from any microorganism or any other species, the only essential requirement being that a signal detectable by an electrode is produced upon generation or depletion of the electro-active material.

Depending on the analyte to be determined, all immunoassay formats (sandwich, competition, inhibition, agglutination) can be performed using the technology of this invention. The limitations that apply to all immunoassay procedures also apply to this process, such as the case where the detection of low molecular weight analytes is not readily achievable using the sandwich assay format.

Immunological interactions are a preferred embodiment of the present invention due to their wide applicability and specificity. It is well known in the art how to obtain polyclonal antisera, monoclonal antibodies and/or fragments and/or derivatives thereof, as well as how to produce genetically engineered antibodies or fragments or derivatives thereof. Another preferred interaction between analyte and specific binding molecule is the one whereby the analyte is a ligand for which the specific binding molecule is the receptor.

The invention described herein is particularly suited to determining the presence or concentration of analyte in complex matrices such as milk and whole blood, traditionally difficult materials in which to conduct assays. The assay incorporates the use of a flow cell or flowing liquid system device or equivalent apparatus allowing the ordered, sequential addition of assay reagents in a reproducible manner. A preferred way of carrying out the method of the invention comprises the use of the apparatus according to the invention. The invention provides an apparatus comprising a flow cell having a means, preferably a channel, through which liquid can flow whereby said means is provided with a working electrode, and at least one of a reference electrode and a counter electrode, a solid phase comprising a specific binding molecule capable of binding the analyte or analyte competitor in close vicinity, preferably less than 1 mm, more preferably less than 0.5 mm from said working electrode, said means having an inlet capable of being connected with one or more sources selected from the group consisting of a first source of a sample suspected of comprising an analyte, a second source of a liquid comprising a substrate, a third source of a liquid comprising a molecule having specific binding affinity for the analyte and a fourth source of a molecule having a label, whereby one or more of these sources may be one and the same, said means is provided with a liquid outlet, said electrodes suitable of being connected to a measuring device and the liquid in and/or outlet suitable of being connected to a liquid flow regulating means to flow the liquid whereby at least part of the solid phase is provided in the form of relatively small elements, preferably magnetic beads. In general the distance of the electrode and solid phase is not more than 10 times the diameter (preferably 5 times) of the magnetic beads. A magnetic bead has an average diameter of 0.1–200 $\mu$m preferably 1–20 $\mu$m. We noticed that the magnetic beads may be heterodispers; viz. the diameter and the shape are not necessary uniform.

A more detailed description of the embodiments of the invention is given below.

DETAILED DESCRIPTION

FIG. 1 illustrates a cross-sectional view through a possible configuration of a flow cell or flowing liquid system immunoassay device which may be attached to a pump and measuring apparatus for test purposes.

Flowing stream systems have a number of potential advantages over the 'dipstick' type devices. In addition to the ease of use associated with flowing liquid methods, the passage of liquid sample and reagents over the transducing element is highly uniform and can be precisely controlled, thus contributing to enhanced device reproducibility. Furthermore by using a means preferably flow channels or similar vessels of appropriate dimensions, the interaction between the various reagent components (receptor protein/antibody and analyte/antigen) can be maximised when compared with the dip-stick type approach and standard static incubation methods (such as ELISA). By enhancing interactions between the various reagent species, a reduction in incubation time and hence a more rapid test system can be developed. Improvements in device sensitivity are also possible using this type of approach.

The basic operating principle of an amperometric biosensor device is the detection of an electro-active species, whose production or consumption can be related to the concentration of a particular analyte.

As an example, the case where glucose oxidase is used as an enzyme label in an electrochemical immunoassay system can be considered. In the presence of the enzyme substrate (glucose) under appropriate conditions, glucose oxidase enzyme will oxidise glucose and transfer electrons to dioxygen, forming the electrochemically active compound hydrogen peroxide. Hydrogen peroxide can be oxidised at a suitable electrode surface poised at an appropriate voltage against a standard reference electrode (typically +0.05–1.0 V, preferably +50–800 mV, more preferably +50–200 mV, versus a silver/silver chloride reference). Electrons are transferred from the hydrogen peroxide to the electrode and associated circuitry, resulting in a current that can be measured amperometrically using suitable monitoring equipment. Other enzyme labels can be used that result in the production or consumption of an electro-active species and incorporating detection of said species at an electrode poised at an appropriate potential (positive, zero or negative) versus an appropriate standard electrode. Therefore preferably the label is bound to the analyte competitor or analyte binder and therefore not directly to the solid phase.

A major drawback of flowing liquid or flow injection systems, incorporating analyte detection using enzyme labels, is that the continuous flow of liquid serves to draw the material to be detected away from the transducer site. This will result in a decrease in system sensitivity. This is a particular problem when using flowing liquid or flow injection techniques in conjunction with electrochemical detection methods. This problem is reduced using the technology of this invention for the reasons described below.

ADVANTAGES OF THE INVENTION

This invention describes the use of low-cost disposable thick-film screen-printed electrodes combined with flowing streams or flow injection analysis for the detection and quantification of trace analytes in process liquids. The current device and assay design has been shown to result in improvements of importance to at least 7 aspects of operation of such set-ups operated as electrochemical affinity sensors.

1) Due to the nature of the design of the assay procedure and device, the electrochemically active species to be detected (e.g. hydrogen peroxide) is effectively confined to a layer that is in close proximity to the surface of the transducing element. This factor acts to reduce losses in the electrochemically active species caused by flowing liquid stream transport effects. The material therefore has a greater opportunity to interact with the transducing element before being transported from the system.

2) The nature of the design of the assay procedure and device, ensures that, in addition to the electrochemically active species accumulating in the vicinity of the transducer, the enzyme label; the electrochemically active species is also located in the same vicinity.

3) Signal-noise ratios could be markedly reduced when operating the device as a 2 electrode, rather than a 3 electrode system. In a 2 electrode system, the reference electrode serves as both a reference and counter electrode, unlike a 3 electrode system, where working, reference and counter electrodes are provided. Further device improvements were possible by incorporating 2 working electrodes into the device design, whereby one of the working electrodes (primary electrode) is in close vicinity to the solid phase material, allowing quantification of both the Faradaic and non-Faradaic response of the system, whereas the other electrode serves as a compensator electrode, allowing the non-Faradaic background current to be subtracted from the primary electrode response.

4) The particular design of the device and assay format results in the generation of stable and reproducible signals, allowing signal measurements as initial velocities (measured as nA per second) to be recorded. This rapid measurement technique will allow a reduction in total assay time.

5) The combination of flowing stream or flow injection techniques with screen-printed thick-film sensor electrodes serves to minimise problems associated with system fouling, thus leading to an improvement in device reproducibility.

6) The design of the flow injection/flowing stream system and assay method is such that the obligatory washing steps, necessary in almost all immunological assay formats, can be performed using the substrate solution. The practical implications are that a time consuming extra step in the assay procedure can be omitted, thus further decreasing the total assay time. Electrochemical detection can commence after the substrate washing step. The design of the assay device is such that a minimal amount of substrate solution is required for the washing operation.

7) Screen-printing methodology represents a means of reproducibly mass-producing sensor devices. However, it is well known that variances between batches of screen-printed sensor devices can occur. For that reason, it has proved necessary to implement a standardisation procedure prior to assays being performed with each batch of cards.

The following scheme is proposed for the development of a commercial system. A number of sensor devices from each batch of cards can be tested as negative and positive controls at the production facility. By determining the signals from these cards at predetermined times, or by measuring the initial substrate conversion velocities obtained from a range of standard samples, the data generated can be employed to predict the behaviour of a particular batch of cards. The data can be programmed into a calibration card supplied with the sensor cards in a test kit. The card is programmed to set the measuring apparatus to a particular zero level. A simple software programme would allow the measuring device to consider samples yielding signals with a given degree of deviation from this zero setting to be either positive or negative with respect to the amount of analyte in the sample.

This is a simple process that has been used in commercially available enzyme electrode systems. The current invention relates to the case where pre-calibration of the system using enzyme-binding component sensor devices drawn from a particular batch is undertaken. This approach enables an end-user to perform a single test with a single sensing card, thus negating the need of calibrating the device every time a new test is performed.

FLOW CELL OR FLOWING LIQUID SYSTEM DESIGN

The following equipment description serves as an example only. This invention covers all types and configurations of flow cell and flowing liquid systems that can be constructed and employed as per the other information provided in this specification.

The flow cell or flowing liquid system can be constructed such that a thick-film screen-printed electrode card can be mounted in place within the structure. The card is clamped or placed in the cell in such a way that sample liquid entering the system first encounters counter, working and then reference electrodes. A suitable seal or sealing method is used to prevent leakage of assay reagents during passage of the flowing streams. FIG. 1. illustrates a schematic cross-section of a typical flow cell or flowing liquid system device.

The flow cell or flowing liquid system can be modular in design. The actual sensing area comprises a working electrode and an immobilisation support. Immunological reagents are immobilised onto this solid support. This support can be made of a suitably porous polymeric material, such as a flat-sheet nitrocellulose or nylon membrane and is ideally constructed such that the majority of the immunological reaction takes place on the side of the support that is positioned over and faces the transducing area.

A card so-prepared is mounted into the modular flow cell or flowing liquid system such that the electrodes are positioned in a hollow means e.g. channel or similar shaped vessel where fluid transport can occur, preferably in a predominantly non-turbulent manner, once the pumping or wicking of solution is started. Clamping of the card into the flow cell or flowing liquid system apparatus serves to maintain the solid phase support in it's position relative to the working electrode.

The flow cell or flowing liquid system device is further constructed in such a way that electrical contact can be made with electrically conducting contact pads that connect the electrodes to the measuring device.

A pump can be connected to either the inlet or the outlet of the flow cell or flowing liquid system device such that liquid is either pumped into or sucked out of the system in an ordered and reproducible manner. The system is then ready for testing.

A flow of sample is guided across the sensing card through the flow cell. Analytes present in the test sample will bind to the specifically impregnated immunological support. The flow cell or flowing liquid system is equally suited to perform both types of inhibition assay, sandwich assays and other types of assay.

The pumping of a sample liquid across the sensing card will result in a specific binding reaction between the immobilised binding component and any analyte present in the sample, provided that appropriate conditions are applied. After the passage of a fixed amount of sample, a valve is switched such that substrate solution of a appropriate concentration is passed through the system. The presence of immobilised tracer enzyme will result in the production or consumption of electrochemically active material. Given that the reaction site of the immunological support is faced towards the working electrode, the majority of electroactive material will be formed or consumed in between the support and working electrode surface, thus 'trapping' the product of the enzyme reaction in the vicinity of the working electrode. This serves to increase the time that this material is in close contact with the working electrode surface and therefore increases overall device sensitivity.

Before any considerable amount of electrochemically active material is formed or consumed, the substrate solution will act as a washing buffer, rinsing the immunological support and removing non-bound and interfering material from the flow cell or flowing liquid system device to a waste reservoir. Actual measurement is started an appropriate number of seconds after the substrate solution, acting as wash buffer, first reaches the support and electrodes. Total assay times of less than 5 minutes have been achieved using this type of approach.

Measurement at this point can be carried out in at least too ways. Either the flow of substrate into the flow cell or flowing liquid system is halted and the system is left for a fixed period of time to allow a certain amount of material to be formed or consumed, or the initial velocity of substrate conversion by the enzyme is determined. This latter approach enables one to perform a more rapid test since no waiting for accumulation of end-product is necessary. Both approaches indicate the amount of enzyme present on the solid-phase support and so are indicative (either directly or indirectly) of analyte concentrations in the test sample.

Since there can be variability between batches of screen-printed electrodes, a small number of cards can be taken from a production batch of cards and used to calibrate the system. In this way, the supply of just one calibration card with each batch of test cards is all that is necessary for calibrational purposes. The calibration card is programmed to set the measuring apparatus to a certain zero level. Software is then used to determine whether the initial signal velocity profile obtained for a particular test sample is higher or lower than the calibration card value. The device readout will record a positive or negative readout accordingly.

The flow cell or flowing liquid system device, sensor card and test procedure also allows quantitative data to be obtained. A co-supplied set of standard sensor cards enables an end-user to create a standard calibration curve. An unknown sample can then be run in the flow cell or flowing liquid system device and the signal generated can be compared to the standard curve and the concentration of specific analyte determined.

In the case where a solid phase (e.g. nitrocellulose membrane) is used, the fixing of the sensor card into the flow cell or flowing liquid system acts to retain this material at the working electrode surface.

Process fluids are introduced to the flow cell or flowing liquid system using a suitable pump (e.g. peristaltic pump) capable of delivering liquid flow rates, typically between 0.05 and 1.0 ml per minute.

Liquid flow devices have previously been described as methods of choice for improving assay sensitivities and reducing assay times. The use of enzyme electrodes for the electrochemical detection of specific analytes in process liquids is also very well known, the specificity of such devices being reliant on the nature of the enzyme system chosen. Electrodes prepared from a variety of suitable conducting materials and in a variety of sizes and configurations are used. Screen-printing as a means of manufacturing electrodes is of increasing interest given the relatively low costs involved and high volume throughputs that can be achieved. Data, obtained from approaches described in this patent, showed that a combination of electrochemistry, immunology, screen-printed electrode systems in flow cell or flowing liquid system formats yielded test systems of greater reproducibility and sensitivity than any other device formerly presented. An additional advantage is that the assay systems herein described required no toxic or otherwise unsafe substance.

ELECTRODE DESIGN

A 3 electrode design card was produced using standard screen-printing technology.

Both the working and counter electrodes were fabricated from carbon based ink paste. The reference electrode, a silver/silver chloride electrode was fabricated using a commercially available silver/silver chloride ink.

The electrodes were designed in such a way that, once mounted in the flow cell or flowing liquid system device, the liquid flows in an orderly manner across each of the electrodes in turn.

Basal tracks, used as a means of connecting each electrode to the potentiostat and monitoring device, were fabricated from a suitable conducting material, preferably ink. These tracks were designed in conjunction with the flow cell or flowing liquid system in order to facilitate simple connection to the potentiostat and monitoring device.

Once the system has been fully assembled, the whole immunological sequence of events will take place inside the flow cell or flowing liquid system at the surface or immediate vicinity of the working electrode.

The flow cell or flowing liquid system may incorporate connectors to allow simple attachment to a pumping device. The cell body can be made of any suitable inert material. Polymeric materials such as perspex appear particularly suited for this purpose. The flow cell or flowing liquid system can be made in two parts to allow introduction and removal of sensor cards into the flowing liquid streams.

Surprisingly it was found that the use of carbon ink containing a platinum group metal to screen print working electrodes was found to have beneficial effects on recorded signals. Glassy carbon working electrodes e.g. used in U.S. Pat. No. 4,978,610 have a great disadvantage. The operating potential has to be relatively high in order to measure electrochemical active species as a result of an enzymatic reaction. Even at elevated potentials(+700 to +100 mV) the detection of $H_2O_2$ is almost if not at all impossible. It is therefore that in these systems a mediator has to be used. This mediator is actively involved in the enzymatic reaction and is measured in its oxidised or reduced form at the glassy carbon working electrode surface. Analyte measurements in these systems are solely dependent on the use of a mediator like e.g. ferrocene and its derivatives. The use of carbon inks containing a platinum group metal, to screen print working electrodes in this invention eliminates the need for toxic mediators.

It also allows the operating potential to drop to values around 0 to +200 mV. In the case were Glucose Oxidase is used as the marker enzyme the end product $H_2O_2$ can be measured directly at the working electrode surface at lowered operating potentials and without the need for a mediator. Especially the drop in operating potential was surprisingly found to have a dramatic impact on the background electrical signals recorded. This can be explained by the fact that especially in complex matrices like whole blood, milk or soil samples electrochemically active species are omnipresent thus causing an a-specific electrical current at elevated operating potentials. Dropping the operating potential to 0 to +200 mV dramatically reduces these background currents.

As will be appreciated also other ways of producing carbon electrodes are known on basis of carbon of graphite particles wherein according to the present invention platinum group metal particles are present e.g. by adsorption or deposition on the carbon particles which will form the working area i.e. electrically conductive layer of the carbon electrode.

Examples of suitable platinum group metals are platinum, palladium or rhodium preferably rhodium is used. In general 0.1%–20% by weight of the platinum group metal is present preferably 0.5–15% by weight. The platinum group metal may for example by deposited on the carbon by vapour phase deposition, electrochemical deposit or by adsorption from a colloidal suspension to form finely divided metal particles on the carbon.

EXAMPLE 1

Strips of nitrocellulose membrane were cut to the exact size of 0.4×0.9 cm. Strips were soaked in a solution of 5 mg/ml PBP (penicillin binding protein) in buffer (0.1M phosphate buffered saline (PBS), pH 7.4). The strips were left to soak for 1 hour at ambient temperature.

After incubation, strips were blocked in a 2% w/v bovine serum albumin (BSA) solution in PBS buffer (pH 7.4) for 1 hour at ambient temperature.

Individual strips were removed from the blocking solution and incubated for 5 minutes at 64° C. in a 1:2000 dilution of 7-ACA-GOD stock solution in whole milk with or without free analyte (penicillin G) present.

Strips were washed for 20 seconds in PBS and placed onto the working electrode of the screen-printed sensor card.

The card was mounted into the flow cell or flowing liquid system and a 0.1M PBS solution was introduced, pumped at a constant rate through the flow cell. The working electrode was poised at a potential of +350 mV and the system allowed to achieve electrochemical equilibrium. A 0.1M glucose solution in 0.1M PBS/0.1M KCl was then pumped into the system. The flow was halted after 60 seconds. The electrochemical response of the system was monitored throughout this period.

Data obtained using this approach are presented in table 1 Results can be expressed as total current increase in $\mu$A over a given time interval or can be interpreted as current increase per unit time ($\mu$A/sec).

Measuring the initial response/time profile of the system is indicative of β-lactam concentration in the test sample and reduces the total assay time of the process.

TABLE 1

| Batch | Penicillin conc. (ppb) | Absolute responce ($\mu$A) Mean (CV) | % of 0 ppb | Velocity (nA sec$^{-1}$) Mean | % of 0 ppb |
|---|---|---|---|---|---|
| Overall | 0 (5) | 0.131 (27.3) | 100.00 | 0.411 (41.7) | 100.0 |
|  | 10 (3) | 0.064 (17.7) | 49.00 | 0.151 (32.0) | 36.76 |
|  | 100 (4) | 0.057 (70.2) | 43.26 | 0.135 (64.9) | 32.92 |
|  | blank (6) | 0.003 (n/a) | 2.45 | 0.039 (n/a) | 9.42 |
| Batch 1 | 0 (3) | 0.141 (26.6) | 100.00 | 0.511 (23.4) | 100.00 |
|  | 10 (0) | — (—) | — | — (— | — |
|  | 109 (2) | 0.087 (35.8) | 61.70 | 0.209 (12.6) | 40.90 |
|  | blank *(4) | 0.004 (n/a) | 2.48 | 0.159 (n/a) | 31.10 |
| Batch 2 | 0 (2) | 0.115 (32.7) | 100.00 | 0.261 (45.5) | 100.00 |
|  | 10 (3) | 0.064 (17.7) | 55.90 | 0.151 (32.0) | 57.85 |
|  | 100 (2) | 0.026 (21.8) | 22.71 | 0.062 (5.7) | 23.56 |
|  | blank (2) | 0.003 (n/a) | 2.18 | 0.000 (n/a) | 0.00 |

Table 1: Data for nitro-cellulose incubation studies. Results are recorded as mean values of n repeat experiments (where n is listed in brackets). Velocity was measured over a time interval of 200 sec.; absolute response values were recorded over 500 sec.; results are also expressed as percentage of the signal of the positive control (0 ppb=no inhibition). CV values, in percent are recorded in brackets.

Results: Example 1:

Nitro-cellulose strips were prepared in two separate batches. The data are recorded as 'Overall' (batch 1+batch 2) and batch 1 and batch 2 and shown in Table 1. Responses are recorded as 'absolute response' values, whereby the total current change is measured from the time that the glucose substrate reaches the WE to a time 500 sec. after this point. Responses are also recorded as 'velocities' whereby the maximum current versus time slope is measured during the period of glucose flow across the working electrode surface (expressed as nA/sec). Results are also expressed as a percentage of the signal of the zero ppb penicillin positive control, that is, the zero inhibited response that therefore yields a 100% response value.

EXAMPLE 2

Strips of nitrocellulose were cut to the exact size of 0.4×0.9 cm. Strips were soaked in a solution of 5 $\mu$g/ml of monoclonal anti-gentamycin antibody in PBS buffer pH 7.4, for 1 hour at ambient temperature.

After incubation, strips were blocked in a 2% w/v BSA solution in PBS(pH 7.4) for 1 hour at ambient temperature.

Individual strips were removed from the blocking solution and mounted onto the working electrode surface, thus creating a complete sensor card.

Sensor cards were mounted into the flow cell, the strip of nitrocellulose being held in place by a rubber seal, used to prevent leakage during operation of the flow cell device.

One ml samples of milk were aliquoted, to which were added 25 $\mu$l of a: 1:1000 (A), 1:2000 (B) or 1:2500 (C) dilution of gentamycin-GOD conjugate (prepared with state of the art procedures).

Free gentamycin was then added to each milk sample, yielding solutions having gentamycin concentrations varying between 0 and 1000 ppb.

A pumping device was connected to the flow cell and the prepared milk samples were each tested with a new sensor card mounted in place.

The flow rate through the system was adjusted so that the complete milk sample passed through the system over a 3 minute time period. A 1 minute wash step was then performed with 0.1% w/v Tween in 0.1M PBS (pH 7.4). Immediately after each wash step, 0.5M glucose in 0.1M PBS/0.1M KCl was passed through the flow cell and the electrochemical responses generated were recorded both as absolute values and as initial response-time velocities in nA/sec.

A 1:10 dilution of the MoAb stock solution was used to coat the nitro-cellulose strips. Gentamycin-glucose oxidase conjugate concentrations were varied from 1:4000 (exp.A) to 1:8000 (exp.B) to 1:10 000 (exp. C). Results from these experiments are presented in Table 2.

TABLE 2

| Exp. No. | Gentamycin conc. | Absolute response ($\mu$A) | | Velocity (nA sec$^{-1}$) | |
|---|---|---|---|---|---|
| | | Mean value | CV % | Mean value | CV % |
| A | 0 ppb | 3734 | 1.8 | 37.3 | 5.4 |
| | 10 ppb | 3217 | 3.6 | 36.0 | 0 |
| | 100 ppb | 3050 | 1.2 | 22.7 | 0 |
| | 1000 ppb | 1350 | 13.6 | 8.7 | 38.7 |
| B | 0 ppb | 2655 | 0.2 | 21.5 | 0 |
| | 10 ppb | 2438 | 1.5 | 18.0 | 2.8 |
| | 100 ppb | 2025 | 3.7 | 14.3 | 5.3 |
| C | 0 ppb | 2278 | 4.1 | 14.4 | 11.9 |
| | 10 ppb | 1868 | 2.6 | 10.8 | 10.8 |
| | 100 ppb | 1333 | 3.8 | 6.0 | 3.3 |

Table 2: Data from experiments a, b, c. Results are recorded as mean values of duplicate experiments (a, b) and triplicate experiments (c).

EXAMPLE 3

The purpose of this example is to demonstrate the applicability of the invention to performing highly sensitive assays using the so-called 'endpoint' measurement technique to quantify the level of enzyme activity, hence determining free gentamycin concentration in gentamycin containing milk samples.

The immunological reaction step is performed in a microtiter plate. Using GOD as the enzyme label, the final microtiter well solution will contain hydrogen peroxide, the amount of which is inversely proportional to the amount of free gentamycin present in the sample under uniform conditions (competitive assay approach). This solution is pumped through the flow cell yielding a current peak, the magnitude of which is directly proportional to the amount of hydrogen peroxide present. Since no enzyme label is present in the final solution, no further hydrogen peroxide generation occurs after removal of solution from the microtiter well, thus current peaks, as opposed to current steps are observed on liquid passage through the flow cell.

Microtiter plates were coated in carbonate/bicarbonate buffer pH 9.6 for 1 hour at 37° C., then washed and blocked with 0.5% w/v gelatin in PBS buffer pH 7.4. Plates were either used directly or stored at 4° C. until required.

EXPERIMENTAL PROTOCOL AND RESULTS

Primary incubations with gentamycin-GOD, with or without free gentamycin, and in milk or buffer (PBS pH 7.4) were performed for 1 hour at 37° C. Gentamycin-GOD concentrations were varied between 1:1000 and 1:20 000. All incubations solutions had a total volume of 100 $\mu$l. Plates were then washed in PBS/Tween 20.

Substrate solution (200 $\mu$l of 0.1M Glucose in PBS pH 7.4/0.1M KCl) was then added.

After a given time period for substrate conversion, 150 $\mu$l of solution was pumped through the flow cell using a peristaltic pump set at a constant flow rate of 300 $\mu$l/min. Responses were measured as peak heights in nA or mA. Sensor cards were preconditioned for 5 seconds at 1V prior to operation at +350 mV (versus Ag/AgCl reference/counter electrode). Results are shown below in Table 3.

TABLE 3a

| | Anti-gentamycin | | Gentamycin-GOD dilution | | | | | Substrate Inhibition | Substrate time (min) | Substrate temp. (° C.) |
|---|---|---|---|---|---|---|---|---|---|---|
| | 1:100 | 1:1000 | 1:1000 | 10000 | 1:2000 | Milk | Buffer | | | |
| 1 | | x | x | | | | | 0–200 ppb | 5 | 60 |
| 2 | | x | | | x | | | 0–200 ppb | 5 | 60 |

Table 3a: Experimental parameters used in end-point measurement studies.

TABLE 3b

| Exp. | 200 ppb | 100 ppb | 50 ppb | 25 ppb | 10 ppb | 5 ppb | 0 ppb | blank |
|---|---|---|---|---|---|---|---|---|
| 1 | 6.6 | 5.0 | 7.5 | 6.6 | 9.0 | 5.5 | 100 | 16.9 |
| | (0) | (0) | (11) | (25) | (27) | (18) | (25) | (50) |
| 2 | 25.0 | 28.5 | 28.5 | 15.2 | 10.5 | 12.4 | 100 | 19.5 |
| | (3.7) | (6.7) | (6.7) | (12.5) | (9) | (7.6) | (14.5) | (33) |

Table 3b: Results from end-point measurement experiments nos. 3 & 4. Results are recorded as a percentage of positive signal (0 ppb=no inhibition=100% signal). Bracketed data records CV (%), n is 2–4.

Considerable inhibition of the positive signal was seen for gentamycin concentrations as low as 5 ppb when using a 1.10 000 dilution of gentamycin-GOD conjugate. As expected when using such a low conjugate dilution, inhibited signals were indistinguishable from the background noise generated in the system.

EMBODIMENTS OF AN APPARATUS ACCORDING TO THE INVENTION

Embodiments of will be further explained and illustrated, by way of example, with reference to the accompanying drawings, in which.

In the drawing corresponding elements have corresponding reference numbers.

Figure 1:
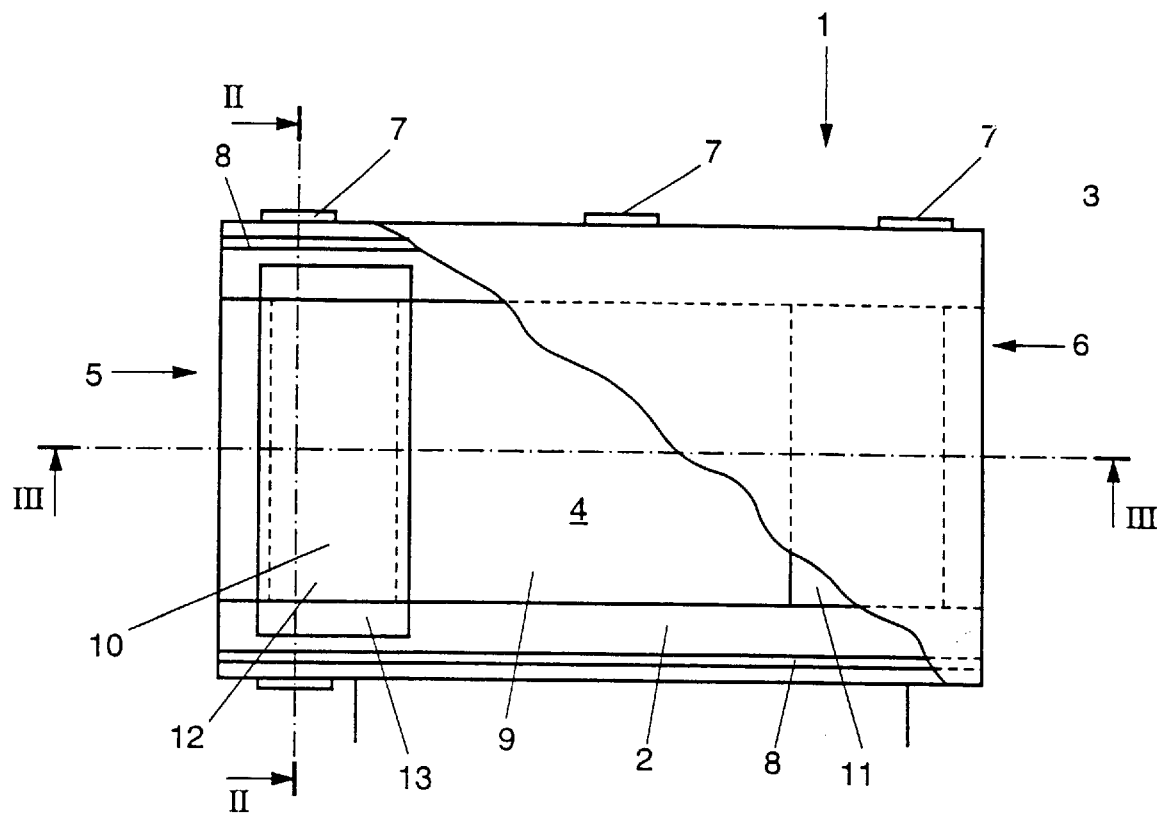
FIG. 1 is an elevational view of a flow cell, the top part partly broken away.
Figure 2:
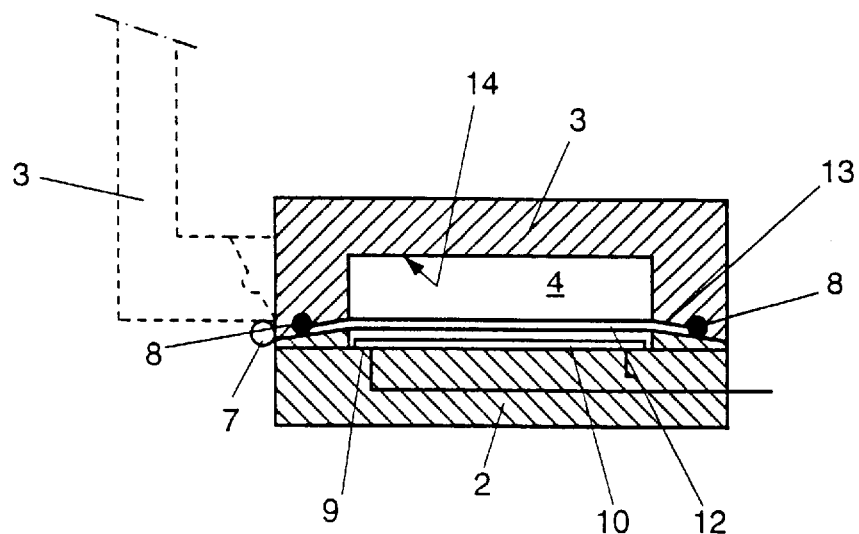
FIG. 2 is a cross-section of a flow cell along the line II—II of FIG. 1.
Figure 3:
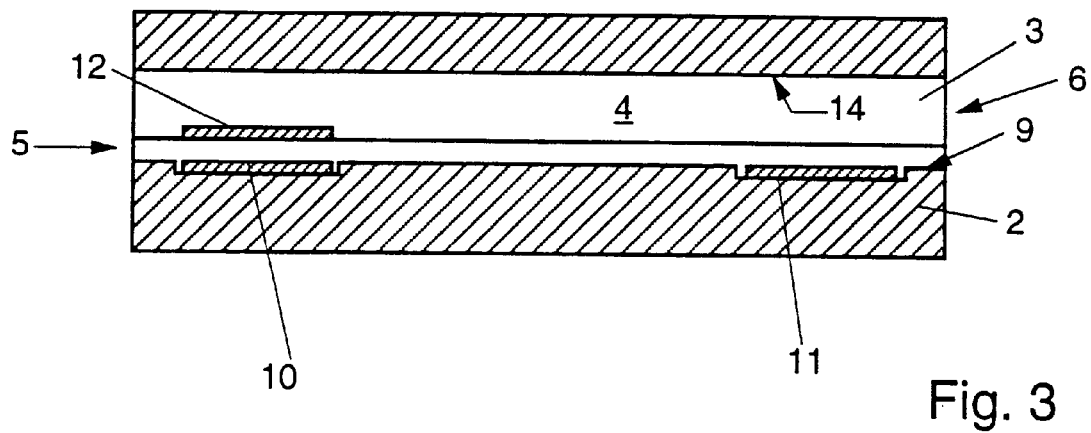
FIG. 3 is a cross-section of a flow cell along the line III—III of FIG. 1.

In FIGS. 1–3, a flow cell 1 is shown, specifically for use in a method according to the present invention. The flow cell 1 comprises a first part 2, further referred to as bottom part 2 and a second part 3, further referred to as top part 3. The flow cells are all shown schematically and are not to scale. Proportions and dimensions can vary. Between the bottom part 2 and top part 3, a channel or similar vessel 4 is enclosed which connects a liquid inlet 5, on one side of the flow cell 1, with a liquid outlet 6 on the opposite side of the flow cell 1. The top part 3 is connected to the bottom part 2 by a hinge 7 along a side of the flow cell parallel to the length of the channel or similar vessel 4. Between the bottom part 2 and the top part 3 a seal 8 is positioned to prevent liquid passing between the parts 2 and 3 during use, other then through the channel or similar vessel 4.

On the bottom, 9, of the flow channel or similar vessel 4, a first electrode 10, to be referred to as working electrode (WE) is positioned near the liquid inlet 5. At least one second electrode 11, a reference (RE) or counter electrode (CE) is positioned on the bottom, 9 of the channel or similar vessel, 4, downstream from the working electrode 10. The, or each second or further electrode can also be positioned upstream or in any other position, distant from the first electrode, such that interference of the electrodes is avoided.

The electrodes are preferably of a screen-printed type and can be either positioned on the channel or similar vessel bottom 9 or, preferably, in a recess in the channel or similar vessel bottom 9, such that the upper surface of the electrodes 10, 11 are flush with the surface of the channel or similar vessel bottom 9, in order to minimise turbulence during use.

Over the working electrode 10, a solid phase 12 is positioned, for example in the form of a sheet of nitrocellulose or any other suitable solid phase. The sheet of solid phase 12 has a width somewhat greater then the width of the channel or similar vessel 4 perpendicular to flow direction thereof. The sheet 12 is provided with opposite side parts 13 clamped between the bottom part 2 and top part 3 when the flow cell 1 is in its closed position (FIG. 2). The sheet 12 is preferably mainly provided with reactive solid phase on the side directed to the working electrode 10, while the working electrode 10 is covered by the sheet 12. During use liquids can pass trough the channel or similar vessel over the sheet 12, between the sheet 12 and the working electrode 10 as well as between the sheet 12 and the channel or similar vessel roof 14 opposite the channel or similar vessel bottom 9, thereby reacting with the solid phase.

The top part 3 can be pivoted to an opened position, shown in broken lines in FIG. 2. In this opened position the channel or similar vessel 4, especially the electrodes 10, 11 and the solid phase 12 are directly accessible. The sheet 12 of solid phase can be taken out of the relevant part 2, 3 and be exchanged for a new sheet 12 of solid phase, after which the top part 3 can be brought in the closed position against the bottom part 2 again, clamping the solid phase in position. In the opened position furthermore the channel or similar vessel 4 forming parts, the electrodes 10, 11 and the seals can be handled, if necessary. This flow cell 1 therefore has the advantage that it can be re-used after exchange of the solid phase, which can be easily achieved.

Figure 4:
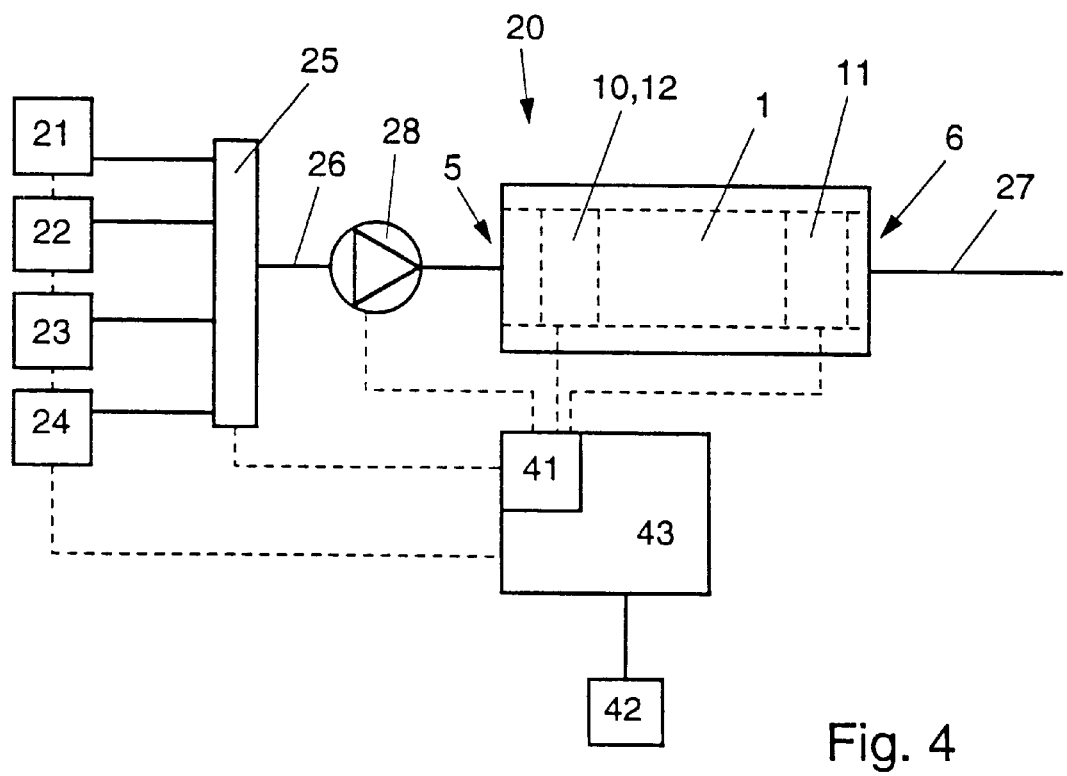
FIG. 4 is a schematic view of an apparatus containing a flow cell according to the invention, in a first embodiment.

FIG. 4 shows a schematic view of an apparatus 20 containing a flow cell 1 according to the invention. The apparatus 20 comprises a first source 21 of a liquid suspected of comprising an analyte, for example milk, a second source 22 of a liquid comprising a substrate, a third source 23 of a liquid comprising a molecule having a specific binding affinity for the analyte and a fourth source 24 of a liquid containing a molecule having a label. The apparatus furthermore comprises a multi-valve 25, connected to the inlet-side with the said sources 21–24. The outlet-side of the multi-valve 25 is connected to a first conduit 26, connected to the liquid inlet 5 of the flow cell 1. A second conduit 27 is connected to the liquid outlet 6 thereof, for discharge of the liquids from the flow cell. In the first conduit 26 a pump 28 is positioned for pumping the liquids from the respective sources 21–24 to and through the channel or similar vessel 4. The pump 28 is preferably of a peristaltic type, capable of very precisely pumping small amounts of liquids, for example as little as 0.1 ml per charge. This enables very accurate dosage of the liquids.

Figure 5:
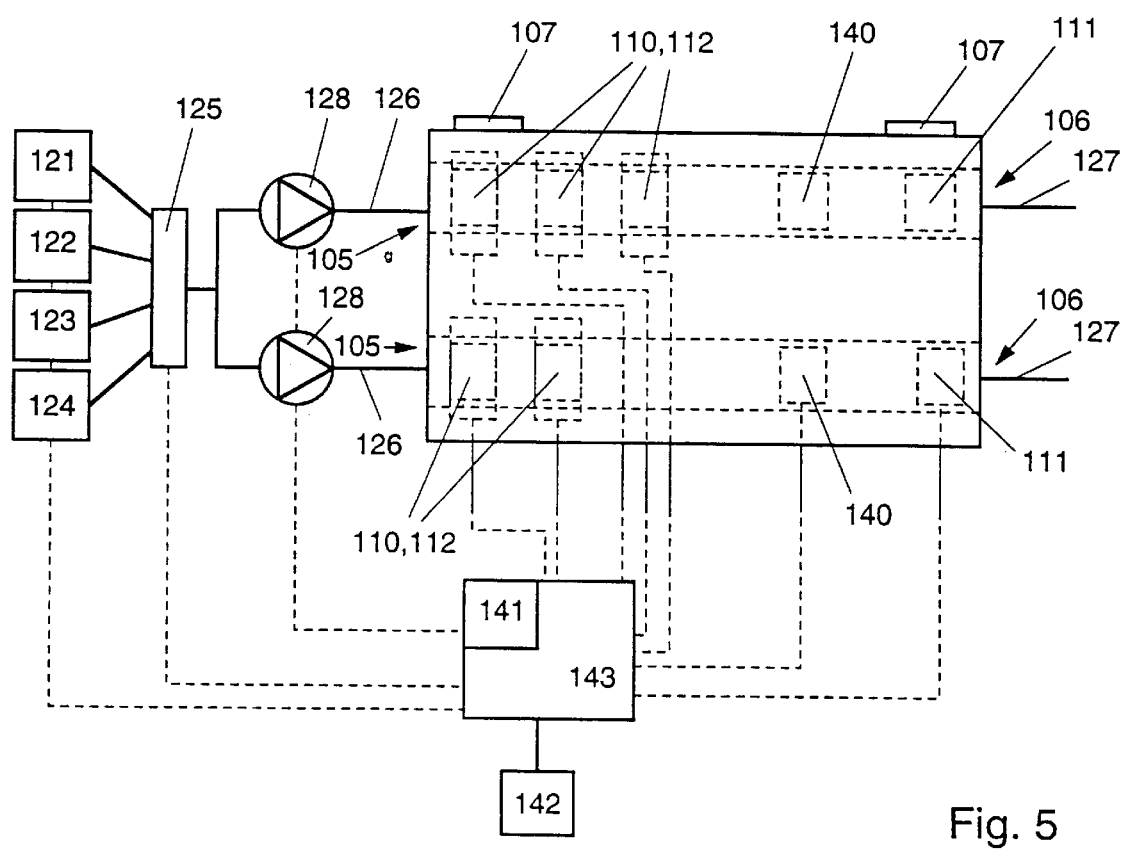
FIG. 5 is a schematic view of an apparatus containing a flow cell according to the invention, in a second embodiment.

In FIG. 5 a second embodiment of an apparatus according to the invention is shown schematically, wherein a flow cell 101 is provided with two parallel channels or similar vessels 104, each channel or similar vessel 104 provided with a series of measuring electrodes 110 and corresponding solid phases 112. Each solid phase 112 is intended for detecting a specific analyte. In this embodiment a mixing apparatus 130 is connected to at least two sources, in the embodiment shown as an example the first 121 and second source 122. In the mixing apparatus 130 a combination can be obtained of a specific dosage of the liquid from the connected sources, for example for pre-labelling of the analyte in the sample.

The outlet-side of the mixing apparatus 130 is connected to an inlet-side of the multi-valve 125, as are the other sources 123 and 124. The outlet side of the multi-valve 125 is connected to the liquid inlets 105 of the respective channels or similar vessels 104 of the flow cell 101. It will be apparent that the channels or similar vessels 104 can also be provided in different flow cells, whereas any number of measuring electrodes can be positioned in any one of the channels or similar vessels.

In the channels or similar vessels 104 of the flow cell 101, a counter electrode 140 is positioned between the working electrode 110, at least downstream of the last working electrode 110, and the reference electrode 111 for enhancing the results of measurements, especially when high currents and/or high fluctuations in currents require detection.

The electrodes 10, 11 or 110, 111, 140 are connected to a measuring device 41, 141 respectively. Only the measuring device 41 will be described more extensively, the measuring device 141 being comparable to this device 41. The measuring device is provided with means for maintaining an operating potential across the electrodes 10, 11. Furthermore the device 41 is provided with means for detecting current fluctuations, resulting from electrochemical reactions on or near the working electrode 10. The resulting fluctuations are presented by a means of a display 42 connected to the measuring device as, for example, absolute levels of measured current (mA) at a given reference time after initiation of the electrochemical reaction or as changes in the measured current in ($\delta$mA/sec).

Instead of one pump 28, 128 in the first conduit 26, 126 a pump can be positioned in the second conduit 27 or a number of pumps can be positioned in conduits between the respective sources 21–24, 121–124 and the multi-valve 25, 125.

The measuring device can be integrated in a control device 143, further comprising means for operating the sources 21–24, 121–124, the or each pump 28, 128, the multi-valve 25, 125 and/or the voltage over the electrodes 10, 11, 110, 111, 140. This control device 143 is preferably programmable and designed for (semi)automatic operation of the apparatus.

The measuring and/or control device 42, 142, 43, 143 is further provided with means for maintaining a potential difference between at least two of the electrodes, which difference can be positive or negative, relative to the or each working electrode, depending upon the particular reaction. Preferably, the means for obtaining said potential difference is designed for maintaining this difference at a relatively constant level, in order to obtain smooth signal data, which is readily available and interpretable and has a high signal/noise ratio.

Heating and/or cooling systems can be provided for regulating the temperature of the liquids.

Figure 6:
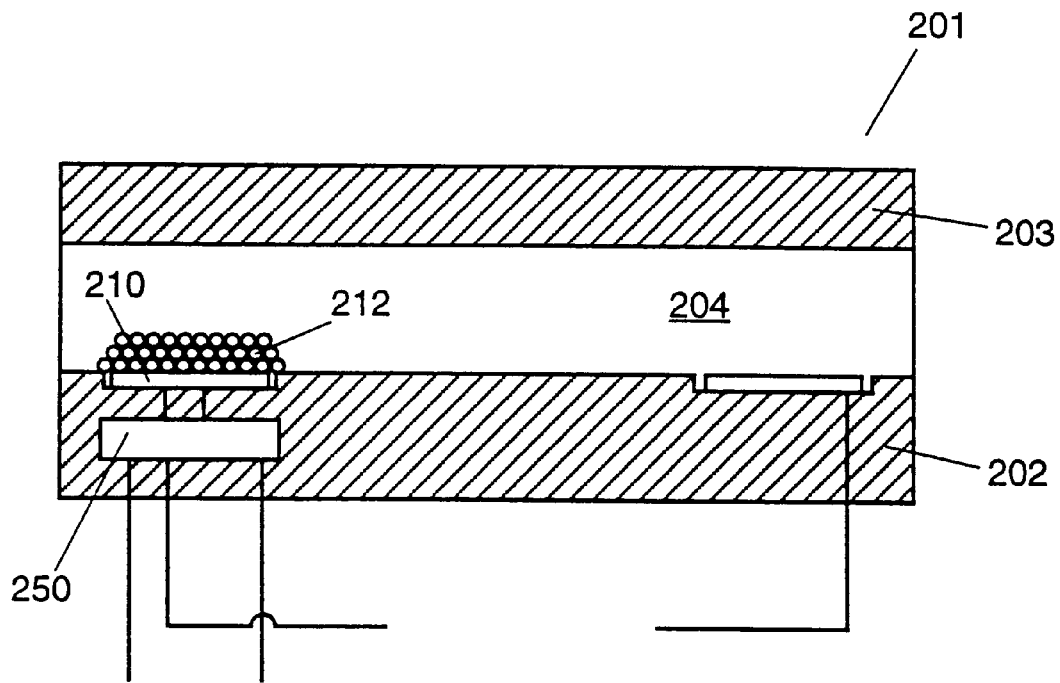
FIG. 6 is a schematic view of a third embodiment of an apparatus according to the invention.

In FIG. 6 a further embodiment of a flow cell 201 is shown, specifically for use in a method according to the invention in which bead or pellet like elements 212 are used for providing the solid phase with said specific binding affinity for the or at least one analyte. The flow cell 201 is similar to the flow cell 1 according to FIGS. 1–3, although the sheet 12 is not present. Corresponding elements have the same reference numbers, added to 200.

Under the working electrode 210, that is at the side thereof facing away from the channel 204 a electromagnet 250 is positioned within the bottom part 202. The magnet 250 is preferably fully covered by the working electrode 210 and has approximately the same size.

Figure 8:
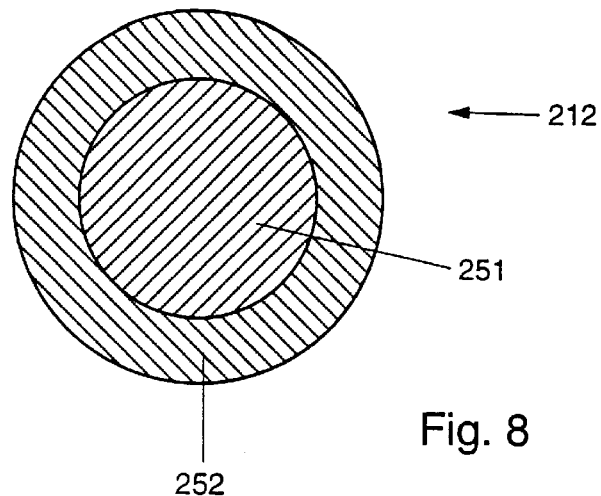
FIG. 8 is a cross sectional view of a solid phase element according for use with an apparatus according to the invention.

In FIG. 8 an element 212 is shown in more detail, in cross section. The element 212 is provided with a metal core 251, covered by a layer 252 of a material having said specific binding affinity for the or at least one analyte. The core 251 is preferably fully covered by the layer 252, although the coverage can be less. Furthermore the layer 252 can consist of a multi-layered structure and can be fully or partially conductive. The material of the layer 252 having said specific binding affinity can extend into the core 251. The core 251 is at least partially made of metal having magnetic properties and can consist of a permanent magnet.

The elements 212 preferably have a diameter between 0–200 $\mu$m, more preferably between 2–50 $\mu$m. In a most preferred embodiment the diameter of all elements is between 2–10 $\mu$m. Such elements can be easily obtained and mixed with any of the liquids, while clogging of the conduits and the channel is easily avoided and sufficient current can be transferred to the working electrode. The elements having a diameter near 0 $\mu$m are considered colloidal metal. The elements 212 are preferably all spheric and of similar size in each batch used for a maximal surface/volume-ratio, but can also be of different form, for example irregular, and of different sizes, for example for obtaining a compact stacking of the elements.

In the position as shown in FIG. 6 the magnet 250 is switched on, whereby the elements 212 are positioned on the working electrode and/or on top of each other, pulled towards the electrode 210 by magnetic force. It will be obvious that in case the elements 212 are themselves at least partially magnetic a metal part 250 can be positioned in the bottom part 202 of the flow cell 201, in stead of the magnet 250, the metal part having magnetical properties. Preferably the magnetic force of the magnet 250 can be adjusted, for example by adjustment of the electrical current over the magnet and/or the distance between the electrode 210 and the magnet 250, such that the number of elements 212 adhering to the electrode 210 can be influenced actively.

Figure 7:
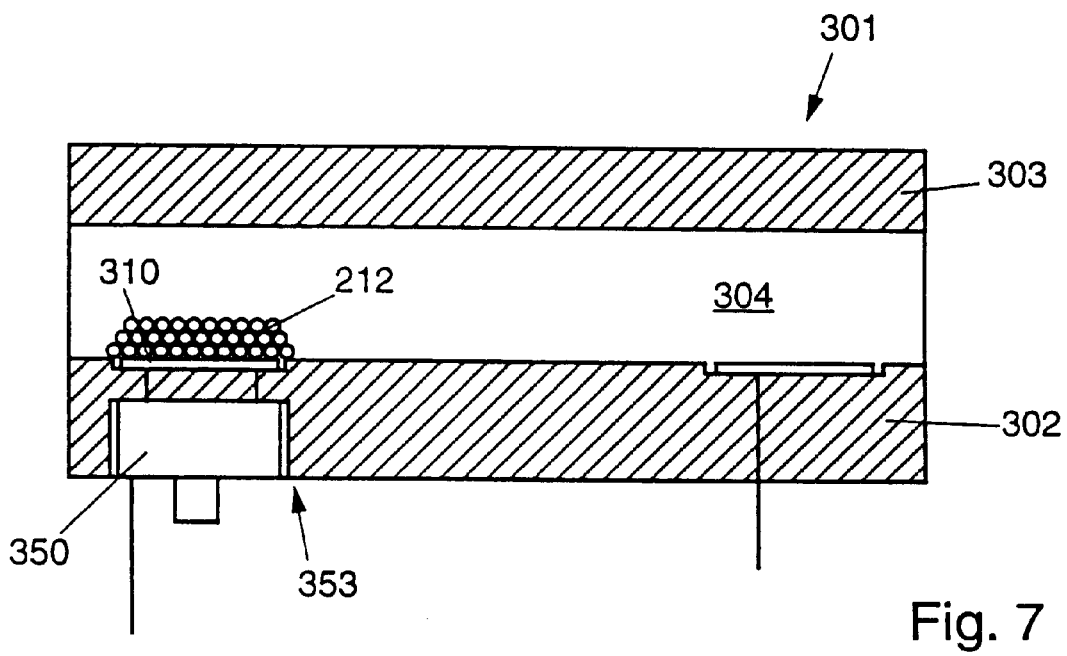
FIG. 7 is a cross sectional view of a flow cell according to the invention according to a fourth embodiment.

In FIG. 7 a further embodiment of a flow cell 301 is shown, similar to the flow cell according the FIG. 6, wherein a permanent magnet 350 is positioned under the working electrode in stead of the electro magnet 250. The permanent magnet 350 is positioned in a recess 353 in the back of the bottom part 302 of the flow cell 301, such that it can be reached form the outside of the flow cell 301. The magnet 350 is thereby removable from the recess 353. In the position shown in FIG. 7 the elements 212 are forced against the working electrode 310 by a magnetic force exerted thereon by said magnet 350.

Figure 9:
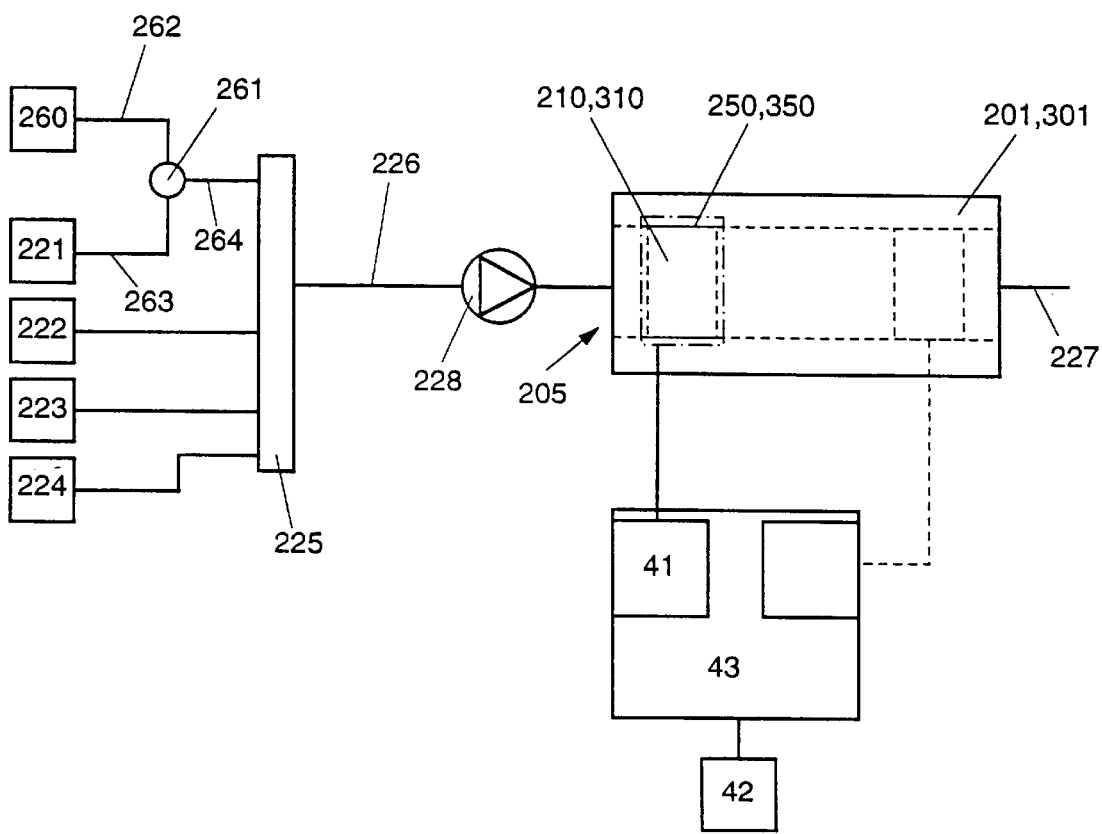
FIG. 9 is a schematic view of an apparatus containing a flow cell according to FIG. 6 or 7.

In FIG. 9 a schematical view of an apparatus according to the invention is shown, comprising a flow cell 201 according to FIG. 6. However, a flow cell 301 according to FIG. 7 could also be used with such apparatus. Where necessary, differences in use of both embodiments will be indicated.

The apparatus shown FIG. 9 comprises a flow cell 201, a first source 221 of a liquid suspected of comprising an analyte, for example milk, a second source 222 of a liquid comprising a substrate, a third source 223 of a liquid comprising a molecule having a specific binding affinity for the analyte and a fourth source 224 of a liquid containing a molecule having a label, and a fifth source 260 comprising said elements 212, for example in a liquid. In the embodiment shown a mixing means 261 is coupled to said fifth source via first coupling means 262 and to the first source via second coupling means 263. In the mixing means 261 the elements 212 are brought sufficiently, preferably in full contact with the sample from the first source 221, in order to provide for sufficient time for the analyte to bind to the solid phase 212, that is to the layer 252. Since the elements 212 are basically spherical, they have a relatively large outer surface and therefore a high binding capacity. The or each mixing means 261 can be static means, such as a T-shaped connecting element, a tube like element having sufficient length for providing a flow time sufficient for said binding or container shaped means in which a specific sample from said first source 221 and a specific amount of elements 212 are brought into contact for a specific time. Further more the mixing means can be dynamic means such as an electrical mixer for providing relative thorough mixing of the sample and the elements in a relative short time. Such dynamic mixing means can be advantageous specifically when the it is difficult to obtain full contact between the elements 212 and the analyte.

It will be obvious that more then one of the sources can be connected to the mixing means, either parallel or sequential. This could for example be advantageous when the apparatus is in use for a test of the concurrent type.

The apparatus furthermore comprises a multi valve 225, connected on the inletside with the said sources 222–224 and with a third connecting means 264 of the mixing means 261. The outletside of the multivalve 225 is connected to a first conduit 226, connected to the liquid inlet 205 of the flow cell 201. A second conduit 227 is connected to the liquid outlet 206 thereof, for discharge of the liquids from the flow cell. In the first conduit 226 a pump 228 is positioned for pumping the liquids form the respective sources 222–224 and the mixing means 261 to and trough the channel 204. The pump 228 is preferably of a peristaltic type, capable of very precisely pumping small amounts of liquids, for example down to 0.1 ml per charge. This enables very accurate dosage of the liquids.

During use first a liquid from the mixing means 261 is fed through the channel 204. The magnetic means 250, 350 are thereby either switched on when a flow cell 201 according to FIG. 6 is used, or brought into the recess 353 in the vicinity of the working electrode 310 when a flow cell 301 according to FIG. 7 is used. During flow through the channel 201, 301 a number of the elements 212 is drawn to the working electrode 210, 310 by the magnetic force and will be positioned on the surface of the electrode 210, 310 and/or on top of each other. Then further necessary steps are taken, for example rinsing, labelling or the like as described here above, after which the actual measurement of the currents from the solid phase, that is the elements 212 can be carried out. After conduct of the measurements the elements 212 can, if necessary be removed from the channel 204, 304 by switching off the magnet 250 or removing the magnet 350 from said recess 353 and for example rinsing the channel 204, 304. Since the magnetic forces will no longer retain the elements 212 on the electrode 210, 310, damage of the electrode will be avoided and the flow cell 201, 301 can be cleaned and re-used.

It will be obvious that a flow cell containing magnetic or similar positioning or retaining means for the elements constituting or carrying solid phase, which elements can be fed through the channel by a liquid can have several channels and/or several electrodes such as a number of measuring electrodes, working electrodes and reference electrodes. The positioning or retaining means can be for example constituted by rims or recesses on top of the working electrode against which rims or in which recesses elements 212 can be caught and retained, whereby the elements 212 do not necessarily have a metal, magnetisable core. Such a flow cell can be cleaned by a counter flow through the channel.

The elements 212 can be conductive, such that a current is easily transferred between the elements and to the measuring electrode. The conductivity of these elements is preferably higher then the conductivity of the liquid in the channel when the relevant data is obtained.

Figure 10:
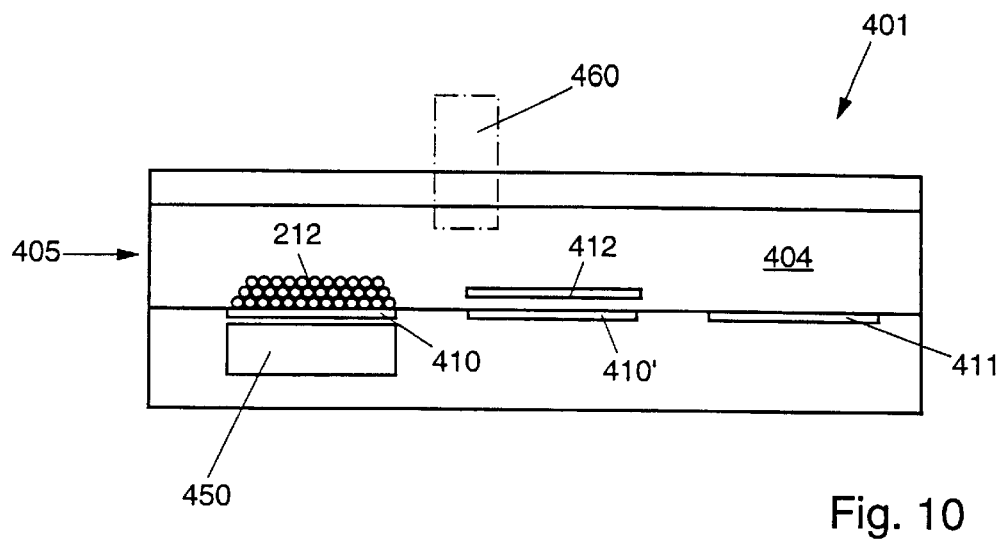
FIG. 10 is an alternative embodiment of a flow cell according to the invention.

In FIG. 10 a still further embodiment of a flow cell 401 according to the invention is shown, which is basically a combination of flow cells described here above. In this embodiment the flow cell 401 is provided with a magnet 450 under a working electrode 410 positioned near the inlet 405 of the channel 404. A second working electrode 410' is placed downstream of the first working electrode 410. A sheet 412 of solid phase of a first type is positioned over the second working electrode 410' in a manner as shown in for example FIG. 1. Elements 212, forming or carrying solid phase of similar of a different type as the sheet 412 are fed into the channel 404 and drawn to the first working electrode 410. The same or preferably a second or further analyte is bound by the solid phase sheet 412, over or on the second electrode 410'. Thus two or more analytes of different types can be detected by use of the same flow cell. Positioning the first electrode 410 with the magnet 450 upstream from the sheet 412 ensures that the elements 212 are mainly pulled out of the liquid before arriving at the sheet 412. Therefore, damage of the sheet 412 and interference of the elements and the sheet are readily avoided. A further magnetic means 460 can be positioned directly downstream from the first working electrode 410 for catching any element 212 passing the first electrode 410.

In an embodiment not shown a sheet 412 is positioned over an electrode which is positioned over a magnet. This sheet 412 can prevent damage of the electrode, for example corrosion of other reactive activity resulting from the liquids, or interference of the measurements as a result of such unwanted chemical reactions.

Figure 11:
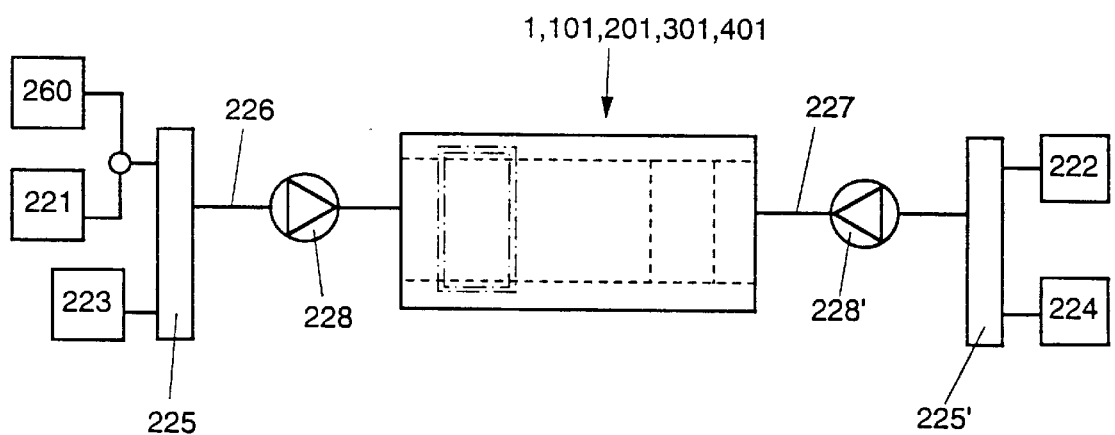
FIG. 11 is a schematic view of an apparatus according to the invention, in a further embodiment.

In an alternative embodiment, as shown in FIG. 11, a number of said sources 21–24, 121–124, 221–224, is connected to the second conduit 27, 127, 227 pump means 28, 28', 128, 128', 228, 228' being provided for directing liquids from said sources in either direction through the channel, depending on the positions of the respective sources. In this embodiment a liquid can be expelled from the channel 4, 104 by feeding the next liquid to said channel, wherein the liquid is forced forward or backward through the channel wherein the liquid can be forced back into its source or can be expelled.

In the embodiments shown the electrodes are positioned in the channel, apart from each other. In a further preferred embodiment, not shown, the electrodes to be used in a flow cell 1, 101 a number of these electrodes, preferably all electrodes (WE, CE and/or RE) are positioned on a card or the like, preferably printed thereon by for example (thick film) screen printing, the card being easily exchangeable. Contact pads or the like are provided within the flow cell for connection of the electrodes to the measuring device.

Part or all of the solid phase can be positioned directly on the working electrode thus providing for easy positioning and removal thereof and for protection of the said electrode, if necessary, against corrosive or otherwise reactive components within the liquids to be fed through the channel or similar vessel.

The invention is in no way limited to the embodiments as shown in the description and the drawings. Many modifications and variants are possible within the scope of the invention as defined in the enclosed claims. For example a number of flow cells or a number of channels or similar vessels can be connected to different sources of at least the first kind, that is sample sources, each cell or channel being connectable to the same second, third and/or fourth or further sources, depending on the particular operation undertaken. On the other hand one cell or channel or similar vessel can be connectable to a number of said sample sources, whereby means are provided for subsequently performing a full measuring cycle on a sample of each first source. These embodiments are for example useful when a number of similar samples require testing for similar analytes. Furthermore, the or each channel or similar vessel can have a different cross-section and flow path. The electrodes can have various forms and can be made of different materials or combinations thereof, mainly depending on the currents to be measured, the space available and the measurement conditions such as the solid phase to be used and the pH of the various liquids used. Different numbers of sources can be connectable to the or each flow cell. Furthermore the flow cell can be constructed in a different form, for example of two or more parts being fully separable from each other. The solid phase and/or the electrodes can be mountable within the channel or similar vessel in different ways, for example integrated onto one carrier which could be maneuvered into place to form a channel or similar vessel. A flow cell having such a construction would not require disassembly and re-assembly of the flow cell in order for replacement of the sensor device. Furthermore the solid phase could be positioned within the channel or similar vessel by other mounting means, for example along one side on the channel or similar vessel base, on the upstream side. A number of suitably prepared flow cells can be positioned in line and mounted in such a way that they can be adjusted to allow subsequent positioning of the flow cells subsequently between the first and second conduit to allow a series of measurements to be performed.

EXAMPLE 4

Detection of Low Levels (ppb range) of Gentamycin in Cow's Milk

Glutaraldehyde activated paramagnetic beads were covalently linked to anti-gentamycin monoclonal antibodies, according to state of the art procedures.

Gentamycin was linked to Glucose Oxidase with a homo-bifunctional linker (BS3- Pierce) according to the manufacturers protocol. A ratio of 1:2:1 for gentamycin:BS3:GOD was used.

Gentamycin-GOD conjugates were immediately frozen at −20° C. after mixing of the components and stored until further use.

Screen printed sensor cards were prepared for the flow cell device in such a way that each card consisted of one rhodonised carbon working electrode, one Ag/AgCl reference electrode and one carbon counter electrode. A new card was used of each assay.

All experiments were conducted at a positive operating potential of 350 mV versus Ag/AgCl in 0.1M KCl. Commingled cow milk was used as the sample matrix. Milk was stored at −70° C. until further use. Positive samples were made from commingled milk spiked with the appropriate gentamycin concentration and were used only once after thawing.

GOD substrate solution contained PBS pH 6.5, 0.1M KCl, 0.1% Tween-20, and 0.5M D-Glucose. Wash buffer contained PBS pH 7.0 and 0.1% Tween-20.

Sequence of Events for Example 1:

1. Milk samples (typical volumes of 200 µl) were incubated in an eppendorf heating block with paramagnetic-beads-anti-gentamycin complex (1 in 1000 dilution) and gentamycin-GOD conjugate (1 in 10.000 dilution). Three different incubation temperatures were examined: 40, 50 and 60° C. Total incubation time: 180 seconds.

2. a sensor card was introduced in the flow cell in such a way that the liquid flow had free access to the electrode surfaces encountering the reference electrode first. Electrical contact with a potentiostat was ensured through electrically conducting screen printed ink pads on the sensor cards (Autolab, Ecochemie Utrecht The Netherlands).

3. A liquid flow was started across the 3 electrode surfaces, passing the sample from 1 across the electrodes.

4. Reacted magnetic beads were captured on top of the working electrode surface by the action of a magnet strategically placed underneath the working electrode. Thus the beads were separated from the milk matrix and reacted GOD was captured in close vicinity to the working electrode surface. Total capture time: 80 seconds.

5. A substrate flow was started across the electrodes and the consequent electrical catalytic current derived from the oxidation of the end product of the GOD/Glucose conversion $H_2O_2$ was measured chrono amperometrically. The amount of current measured per time interval is a measure for the total amount of hydrogen peroxide formed in the enzymatic reaction. Since the immunoreaction on the bead surface is of the inhibition type, the total amount of end product formed in a given time span is inversely proportional to the amount of gentamycin present in the milk sample. Total substrate flow time: 90 seconds Total measurement time: 200 seconds.

Table 4. Absolute catalytic currents measured at different time intervals after substrate addition.

(aCC: absolute catalytic current at t=x seconds after glucose stop. All results in nAmp)

| conc. | Temp. ° C. | aCC at 10 s | aCC at 25 s | aCC at 50 s | aCC at 75 s | aCC at 100 s | aCC at 150 s | aCC at 200 s | aCC at 250 s |
|---|---|---|---|---|---|---|---|---|---|
| 0 ppb | 40 | 85 | 152 | 204 | 229 | 244 | 256 | 258 | 258 |
| 0 ppb | 50 | 63 | 122 | 20S | 237 | 2S1 | 264 | 271 | 274 |
| 0 ppb | 60 | 72 | 136 | 193 | 214 | 228 | 239 | 243 | 247 |
| 5 ppb | 40 | 44 | BS | 134 | 158 | 174 | 190 | 197 | 203 |
| 5 ppb | 50 | 47 | 10S | 167 | 192 | 207 | 224 | 233 | 238 |
| 5 ppb | 60 | 49 | 86 | 139 | 166 | 182 | 201 | 211 | 215 |

Table 5. Calculated percentages of inhibition between 0 and 5 pb signals at 3 different temperatures.

| | at 10 s | at 25 s | at 50 s | at 75 s | at 100 s | at 150 s | at 200 s | at 250 s |
|---|---|---|---|---|---|---|---|---|
| 40° C. | 48.7 | 44.1 | 34.3 | 31 | 28.7 | 25.8 | 23.6 | 21.3 |
| 50° C. | 25.4 | 13.9 | 18.5 | 18.9 | 17.5 | 15.2 | 14 | 13.1 |
| 60° C. | 31.9 | 36.8 | 30 | 22.4 | 20.2 | 15.9 | 13.2 | 13 |

Table 6. Delta catalytic current for 2 time intervals after glucose flow stop.

ΔCC:delta catalytic current over time interval (x seconds after glucose flow stop) in nA/sec.

| Temp. °C. | ΔCC at 20 s | ΔCC at 30 s |
|---|---|---|
| 0 ppb 40 | 6.8 | 5.3 |
| 0 ppb 50 | 5.1 | 4.8 |
| 0 ppb 60 | 5.8 | S.1 |
| 5 ppb 40 | 3.6 | 3.1 |
| 5 ppb 50 | 4.4 | 4.1 |
| 5 ppb 60 | 3.7 | 4 |

Table 7. Calculated percentages of inhibition between 0 and 5 ppb ACCsignals at 3 different temperatures.

| Temp. °C. | % inhibition at 20 s for 5 ppb gentamycin | % inhibition at 30 s for 5 ppb gentamycin |
|---|---|---|
| 40 | 47.1 | 41.5 |
| 50 | 13.8 | 14.6 |
| 60 | 36.2 | 21.6 |

EXAMPLE 5

Detection of Low Levels (ppb range) of Penicilling in Cow's Milk

For the detection of β-lactam antibiotics, a bacterial penicillin binding protein derived from *Bacillus stearothermophilus* was used.

A standard glutaraldehyde activated paramagnetic beads preparation of 80 mg beads/ml was used.

120 g of PBP was added to 1 ml of bead suspension yielding 1.5 mg PBP/gram beads. Covalent linkage was performed according to standard operational procedures known to the art. This stock solution was kept at 4° C. until further use. 7-ACA conjugates of Glucose Oxidase were prepared by covalent linkage of the β-lactam to GOD with the homobifunctional BS3 linker, commercially available through Pierce.

The following weight ratio's were used: 7-ACA:BS3:GOD=1:2:1 Protein concentration of the β-lactam-GOD conjugate were adjusted to 3.3 mg/ml. Conjugates were stored at −20° C. until further use.

Standard commingled cow's milk samples were spiked with increasing amounts of penicilling for inhibition experiments.

Screen printed sensor cards consisted out of 4 electrodes. One Ag/AgCl reference electrode, two rhodonised carbon working electrodes and one carbon counter electrode. The flow cell was set up in such a way that only one WE was to capture the paramagnetic beads. The second working electrode functioned as a compensation electrode measuring background currents during the total measurement procedure. End results were calculated by the subtraction of electrical non faradaic current measured at the compensatory WE from the catalytic faradaic current measured tat the actual working electrode containing the magnetic beads and the GOD.

The use of a second compesnator working electrode increased the reliability of the measurement especially in the early phase of the measurement just after the potenstiostat is turned on and the system measures relatively high non faradiac currents.

Using two working electrodes dramatically decreases the total measurement time necessary.

Signals were recorded at a positive operating voltage of 350 mV versus Ag/AgCl. using the Autolab Array module (Ecochemie Utrecht), 30 seconds after the flow of substrate was stopped.

Sequence of events for the β-lactam magnetic bead electrochemical immunoassay:

1. To 200 μl of milk sample, 10 μl of PBP-bead suspension and 10 μl of a 1:500 dilution of 7-ACA-GOD conjugate were added. The reaction mixture was allowed to incubate for 4 minutes at 64° C.
2. The samples were then transferred to the receiving end of the flow cell (FIG. 7) and the beads were captured on the surface of the WE (working electrode) by a strategically placed magnet underneath the WE, during a constant flow of 2 ml/min.
3. After the beads were separated from the milk sample a substrate flow was started consisting of PBS, pH 6.5, 0.1% Tween-20, 0.1M KCl and 0.5 M D-glucose. Flow was stopped after 30 seconds.
4. Both signal from the actual catalytic working electrode and the compensatory working electrode were measured simultaneously.

Experimental Results Example 5

Table 8: Experimental results in absolute nA measured at x seconds after stop glucose flow.

ΔnA: difference between 0 and 5 ppb as result of inhibition of signal by free penicillin G.

|  |  | nA at 25 s | nA at 50 s | nA at 100 s | nA at 150 s | nA at 200 s |
|---|---|---|---|---|---|---|
| 0 ppb | mean (n = 4) | 2337 | 1305 | 1061 | 1057 | 1076 |
|  | cv % | 28 | 18 | 9 | 6 | 5 |
| 5 ppb | mean (n = 4) | 1906 | 975 | 755 | 786 | 857 |
|  | cv % | 17 | 9 | 3 | 2 | 3 |
| ΔnA |  | 431 | 330 | 306 | 271 | 219 |

These and many similar variants are to be considered as falling within the scope of the invention.

What is claimed is:

1. A method of determining the presence and/or the amount of at least one analyte in a liquid, the method comprises,
    (a) contacting the liquid suspected of containing an analyte with a labeled analyte, labeled analyte competitor or labeled binder and both an electrode and a solid phase having a binder specific for the analyte under conditions wherein the presence of the label generates an amperometric signal, and
    (b) determining the analyte by measuring the generated signal, wherein the solid phase is less than 1 mm from the electrode and the label is capable of being either directly or indirectly detected by the electrode and wherein at least part of the solid phase comprises magnetic beads, and wherein the electrode has a working area comprising carbon particles containing finely divided platinum-group metal particles.

2. A method according to claim 1, wherein the platinum group metal is rhodium.

3. A method according to claim 1, wherein the magnetic beads have a diameter of from 0.1 to 200 μm.

4. A method according to claim 1 wherein the electrode is a printed electrode or wherein the electrode is fixed into position.

5. A method according to claim 1 wherein the magnetic beads are immobilized using magnetic means such that the label can then be detected by the electrode.

6. A method according to claim 1 wherein the label comprises an enzyme.

7. A method according to claim 6, wherein the enzyme is an oxidase, a reductase, a peroxidase, a redox enzyme or an enzyme which generates a surplus or shortage of electrons.

8. A method according to claim 1 wherein the label generates an electrochemically active species which provides an electrochemical signal detectable by the electrode.

9. A method according to claim 8 wherein the electrochemically active species is hydrogen peroxide.

10. A method according to claim 1 wherein a substantial proportion of the liquid sample is brought into intimate contact with the electrode.

11. A method according to claim 1 wherein the solid phase comprises a binding affinity for the analyte, which is a antibody, an antibody fragment, a receptor, an antigen, a nucleic acid fragment or a ligand for the analyte.

12. A method according to claim 1 wherein a specific amount of labeled analyte is present in the liquid.

13. A method according to claim 1 whereby a labeled molecule with specific binding affinity for the analyte is present in the liquid.

14. A method according to claim 1 wherein the solid phase comprises a molecule having specific binding affinity for the molecule having the label.

15. A method according claim 1 wherein the label is an enzyme and detection of the label bound to the solid phase is effected by contacting the label with a substrate for the enzyme and detecting or measuring a reaction product.

16. A method according to claim 1 wherein the liquid is an emulsion, suspension or a colloidal solution.

17. A method according to claim 1 wherein the liquid is a body fluid or a liquid derived therefrom.

18. A method according to claim 1 wherein the liquid sample is milk or another dairy product.

19. A method according to claim 1 wherein the liquid sample is derived from a food or feed product.

* * * * *